(12) United States Patent
Mertins et al.

(10) Patent No.: US 7,989,501 B2
(45) Date of Patent: Aug. 2, 2011

(54) TREATING RENAL CANCER USING A 4-[BIS[2-[(METHYLSULFONYL)OXY]ETHYL]AMINO]-BENZALDEHYDE

(75) Inventors: Susan D. Mertins, Frederick, MD (US); Susan Elaine Bates, Bethesda, MD (US); David G. Covell, Chevy Chase, MD (US); Geoffrey W. Patton, Wheaton, MD (US); Melinda G. Hollingshead, Frederick, MD (US); Rao Vishnuvajjalla, Rockville, MD (US)

(73) Assignee: The United States of America as represented by the Secretary, Department of Health and Human Services, Washington, DC (US)

( * ) Notice: Subject to any disclaimer, the term of this patent is extended or adjusted under 35 U.S.C. 154(b) by 214 days.

(21) Appl. No.: 12/083,583

(22) PCT Filed: Oct. 14, 2005

(86) PCT No.: PCT/US2005/037152
§ 371 (c)(1),
(2), (4) Date: Apr. 14, 2008

(87) PCT Pub. No.: WO2007/044015
PCT Pub. Date: Apr. 19, 2007

(65) Prior Publication Data
US 2009/0131536 A1      May 21, 2009

(51) Int. Cl.
*A61K 31/136* (2006.01)
(52) U.S. Cl. .................................................. 514/646
(58) Field of Classification Search .................. None
See application file for complete search history.

(56) References Cited

FOREIGN PATENT DOCUMENTS
WO   WO-94/25429   11/1994

OTHER PUBLICATIONS

R & D Focus Drug News (May 2, 2005).*
Sullivan et al., Current Urology Reports, (Jan. 2007), 8/1, pp. 5-11.*
S.D. Mertins et al., "In vitro evaluation of dimethane sulfonate analogues with potential alkylating activity and selective renal cell carcinoma cytotoxicity", *Molecular Cancer Therapeutics*, 3(7), pp. 849-860 (Jul. 2004).
M. Jumaa et al., "Degradation of NSC-281612 (4-[bis[2-[Methylsulfonyl)-oxy]ethyl]amino]-2-methyl-benzaldehyde), an Experimental Antineoplastic Agent: Effects of pH, Solvent Composition, (SBE)$_{7m}$β-CD, and HP-β-CD on Stability", *Journal of Pharmaceutical Sciences*, 93(3) pp. 532-539 (Mar. 2004).
S.D. Mertins et al., "Screening for an Identification of Novel Agents Directed at Renal Cell Carcinoma", *Clinical Cancer Research*, vol. 7, pp. 620-633 (Mar. 2001).
Elderfield et al., "Synthesis of Potential Anticancer Compounds. XIV. Methanesulfonic Acid Ester Analogs of Nitrogen Mustards," *J. Organic Chem. 27*:573-575, 1962.
Carter et al., "In Vivo Efficacy of an Aldehyde Degradation Product of Dimethane Sulfonate (NSC 281612) in an Orthotopic RXF-393 Human Renal Tumor Model," 96th Annual Meeting, Apr. 16-20, 2005, Anaheim/Orange County, CA, American Association for Cancer Research (Abstract No. 1381).
Covey et al., "Preclinical Pharmacokinetics and Metabolism of Benzaldehyde Dimethane Sulfonate (BEN) (NSC 281612)," 96th Annual Meeting, Apr. 16-20, 2005, Anaheim/Orange County, CA, American Association for Cancer Research (Abstract No. 1377).

* cited by examiner

*Primary Examiner* — Phyllis G. Spivack
(74) *Attorney, Agent, or Firm* — Klarquist Sparkman, LLP

(57) ABSTRACT

The present invention features methods of treating a mammalian subject having renal cancer by administration of certain dimethylsulfonate compounds, such as a 4-[bis[2-[(methylsulfonyl)oxy]ethyl]amino]-benzaldehyde. The present invention further features administration protocols and dosing schedules for methods of treating patients having renal cancer and pharmaceutical compositions suitable for use in the treatment methods provided herein.

27 Claims, 4 Drawing Sheets

TREATING RENAL CANCER USING A 4-[BIS[2-[(METHYLSULFONYL)OXY]ETHYL]AMINO]-BENZALDEHYDE

BACKGROUND OF THE INVENTION

1. Field of the Invention

The present invention provides pharmaceutical compositions comprising at least one dimethane sulfonate compound and methods for treating patients suffering from or susceptible to renal cancer by administration of a dimethane sulfonate compound to the patient.

2. Background

Renal cell carcinoma (RCC) in humans is one of the most difficult malignancies to treat. Few effective therapies have been found; presently, only biological therapy offers some minimal benefit for patients with this disease. The mechanism of the extensive drug resistance observed in RCC has not been elucidated, although expression of membrane transporters and metabolism have been suggested. Few antineoplastic compounds have been developed in a specific search for agents active against this disease.

RCC accounts for 3% of all adult male malignancies in the United States and is a clinicopathologically heterogeneous disease that includes several histologically distinct cellular subtypes. A majority of the published evidence suggests that proximal renal tubules are the sites from which malignant RCC cells originate, although a recent study offers evidence that such cells may also originate from distal tubules. RCC also frequently develops in conjunction with polycystic kidney disease and renal allografts, both of which conditions induce a chronic regenerative response.

Certain dimethane sulfonate compounds (e.g., NSC-268965, 280074, 281613, and 281817) were identified as having in vitro activity against RCC tumor cell lines. However, antitumor activity of these compounds in xenograft-bearing mice was only modest. See, Mertins et al. (*Clinical Cancer Research*, (2001) 7:620-633) and Mertins et al. (*Molecular Cancer Therapy*, (2004) 3(7) 549-860). Each of the compounds possess in viva antitumor activity at high dosages and only a few animals were tumor free.

NSC-281612 is a dimethane sulfonate compound which was first prepared in the 1960's as a synthetic intermediate in the preparation of various Schiff base compounds. See, Elderfield, et al., *Journal of Organic Chemistry*. (1962) 27, 573-575, Chaudhari, et al., *Bull. Haff. Instt*. (1975) 3:1, 20-26, and Chaudhari, et al., *Bull. Haff. Instt*. (1975) 3:2, pp 81-90. Elderfield also reports, based on a private communication, that NSC-281612 possesses activity against Dunning rat leukemia (see Elderfield, page 574, left column lines 11-5 from the bottom of the page). No specific data was disclosed.

At present, treatment of renal cell carcinoma has been limited by an absence of selective and high activity anti-tumor agents and methods of treating tumors in a patient. Thus, it would be desirable to provide new therapeutic protocols for treatment of renal cancer. In particular, it would be desirable to provide new administration protocols for dimethane sulfonate compounds which reduce or eliminate renal cancer cells or tumors.

SUMMARY OF THE INVENTION

The present invention provides methods of treating patients suffering from or susceptible to renal cancer by administering to the patient a dimethane sulfonate compound. The present invention further provides dosing schedules for the administration of the dimethane sulfonate compound to the patient which are suitable for reducing or eliminating renal cancer tumors and/or renal cancer cells in the patient. The present invention further provides pharmaceutical compositions comprising at least one dimethane sulfonate compound and a pharmaceutically acceptable carrier or excipient for use in the methods of the invention.

In certain aspects, the invention provides a method for treating a patient suffering from or susceptible to renal cell carcinoma, comprising the step of administering to the patient a 4-[bis[2-[(methylsulfonyl)oxy]ethyl]amino]-benzaldehyde compound which has a non-hydrogen substituent ortho to the aldehyde residue, or a pharmaceutically acceptable salt thereof.

In certain other aspects, the invention provides a method for treating a patient suffering from or susceptible to renal cell carcinoma, comprising:

administering to the patient a compound according to the Formula I:

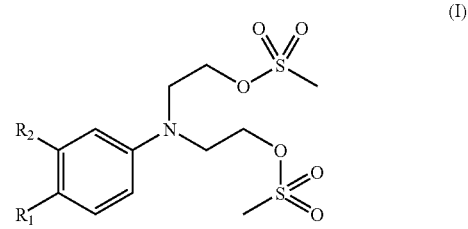

wherein $R_1$ is selected from formyl, $C_1$-$C_4$alkanoyl, $C_1$-$C_4$alkoxycarbonyl, cyano, and aldehyde O—$C_1$-$C_4$alkyloxime; and $R_2$ is selected from $C_1$-$C_4$alkyl, $C_1$-$C_4$alkoxy, and halogen, or a pharmaceutically acceptable salt thereof.

In yet other aspects, the invention provides a pharmaceutical composition comprising at least one pharmaceutically acceptable carrier and a compound according to formula I, or a pharmaceutically acceptable salt thereof.

Other aspects of the invention are described infra.

DETAILED DESCRIPTION OF THE INVENTION

Figure 1:
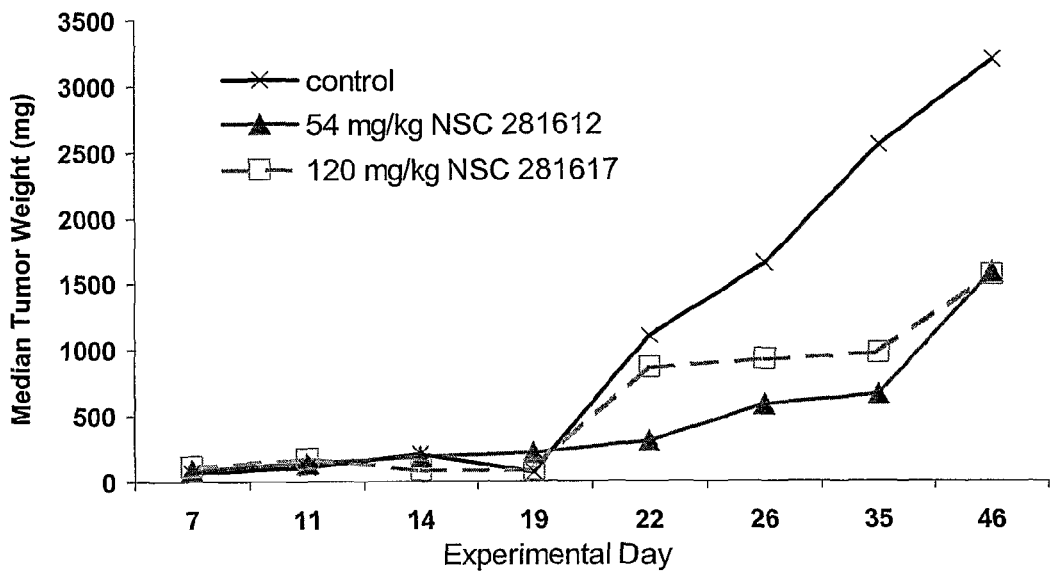
FIG. 1 is a plot of median tumor weight (mg) of subcutaneous A498 human renal tumor xenografts in athymic nude mice at various time points after three fold administration of NSC-281612 or NSC-281617 at four day intervals to mice starting four days after inoculation of one kidney with A498 human renal tumor cells.
Figure 2:
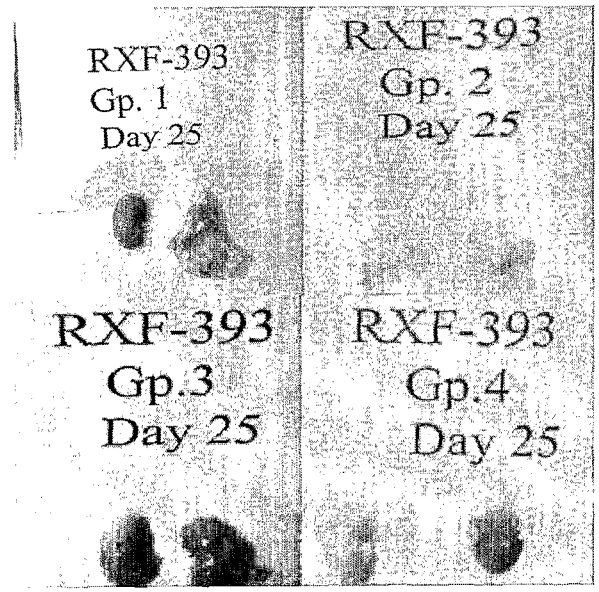
FIG. 2A-2D is a series of photographic images of athymic nude mice kidneys harvested at 25 days post implantation with RXF-393 human renal tumor cells. The mice of Group I (control) were administered five doses of vehicle without NSC-281612 intraperitoneally (IP) every four days starting at day 4, mice of Group II were administered four doses of NSC-281612 intraperitoneally (IP) on every fourth day starting on day 4 wherein the first three doses were 25 mg/kg NSC-281612 and the fourth dose was 8.2 mg/kg NSC-281612 (27% weight loss but no mortality), mice of Group III were administered five 16.8 mg/kg doses of NSC-281612 intraperitoneally (IP) every fourth day starting at day 4 (25% weight loss but no mortality), mice of Group IV were administered five 11.3 mg/kg doses of NSC-281612 intraperitoneally (IP) every fourth day starting at day 4 (20% weight loss but no mortality)

The present invention provides pharmaceutical compositions comprising certain dimethane sulfonate compounds and methods of treating renal cancer by administering said pharmaceutical compositions to a patient suffering from or susceptible to renal cancer.

In certain aspects, a method for treating a patient suffering from or susceptible to renal cell carcinoma is provided in which the method comprises the step of administering to the patient a compound according to Formula I as defined supra, a pharmaceutically acceptable salt thereof or a pharmaceutical composition comprising same.

In certain methods of treatment, compounds of Formula I administered to a patient include those compounds in which $R_2$ is selected from methyl, ethyl, methoxy, fluoro, chloro, and bromo, or $R_2$ is methyl. In other methods of treatment, compounds of Formula I administered to a patient include those compounds in which $R_1$ is selected from formyl, acetyl, cyano, methoxycarbonyl, ethoxycarbonyl, and aldehyde O-methyl-oxime or $R_1$ is formyl. In certain preferred methods, compounds of Formula I administered to a patient include those compounds in which $R_1$ is formyl and $R_2$ is methyl.

In certain other methods of treating patients suffering from or susceptible to renal cancer, the compound of Formula I administered to the patient is a pharmaceutically acceptable salt, hydrate, or solvate. As used herein, a pharmaceutically acceptable salt is an acid or base salt that is generally considered in the art to be suitable for use in contact with the tissues of human beings or animals without excessive toxicity, irritation, allergic response, or other problem or complication. Such salts include mineral and organic acid salts of basic residues such as amines. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)_n$—COOH where n is 0-4, and the like. In certain preferred methods the patient is administered a pharmaceutically acceptable fumarate salt.

Certain methods of treating a patient suffering from or susceptible to renal cell carcinoma comprise the step of administering to the patient a 4-[bis[2-[(methylsulfonyl)oxy]ethyl]amino]-benzaldehyde compound which has a non-hydrogen substituent ortho to the aldehyde residue, or a pharmaceutically acceptable salt thereof. In certain methods, the 4-[bis[2-[(methylsulfonyl)oxy]ethyl]amino]-2-substituted benzaldehyde compound is a fumarate salt. In certain other methods, the 4-[bis[2-[(methylsulfonyl)oxy]ethyl]amino]-2-substituted benzaldehyde compound comprises a non-hydrogen substituent ortho to the aldehyde residue selected from methyl, ethyl, fluoro, and chloro. In certain other methods, the 4-[bis[2-[(methylsulfonyl)oxy]ethyl]amino]-2-substituted benzaldehyde compound is 4-[bis[2-[(methylsulfonyl)oxy]ethyl]amino]-2-methyl-benzaldehyde (NSC-281612) (or fumarate salt thereof), 4-[bis[2-[(methylsulfonyl)oxy]ethyl]amino]-2-methyl-benzonitrile (NSC-716794), 4-[bis[2-[(methylsulfonyl)oxy]ethyl]amino]-2-methyl-benzoic acid ethyl ester (NSC-717120), 4-[bis[2-[(methylsulfonyl)oxy]ethyl]amino]-2-methyl-benzaldehyde O-methyl-oxime (NSC-717121), or a pharmaceutically acceptable salt thereof. Chemical structures for NSC-281612, NSC-716794, NSC-717120, NSC-717121 are as follows:

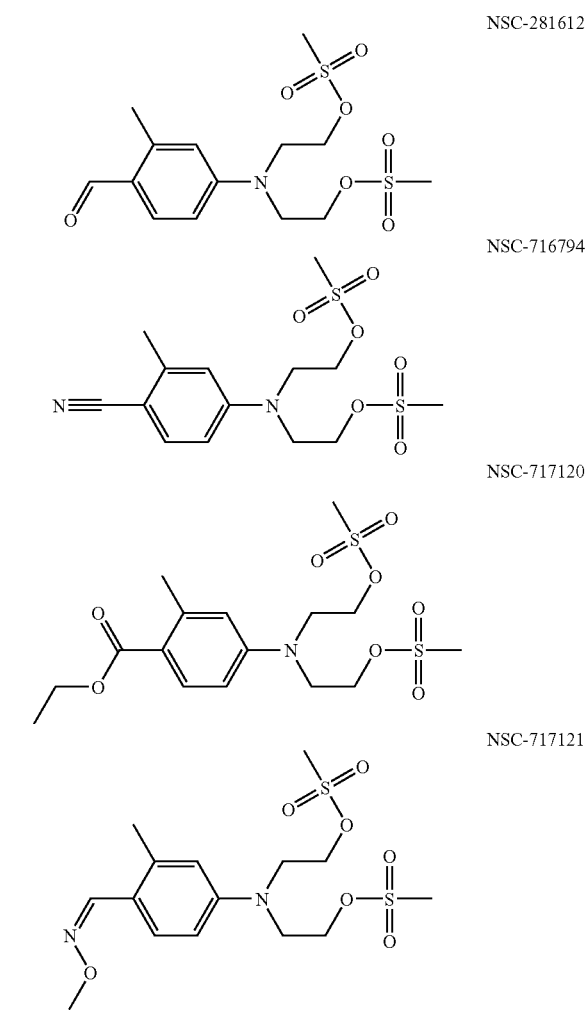

In certain other methods, the compound of Formula I is a pharmaceutically acceptable salt of 4-[bis[2-[(methylsulfonyl)oxy]ethyl]amino]-2-methyl-benzaldehyde.

In the methods of treating renal cancer provided herein, the compound of Formula I can be administered in a single dose, in a series of daily doses or in an intermittent dosing format (e.g., a plurality of doses administered between two and about fourteen days apart or between two and about seven days apart). In certain methods, the administration protocol and compound of Formula I are selected to provide at least a 50% reduction in tumor size, or more preferably at least a 75%, 90%, or 95% reduction in tumor size after completion of the administration protocol. In certain other methods, selection of the administration protocol and compound of Formula I result in a 95% reduction in tumor size, a 99% reduction in tumor size or a substantially complete elimination of the tumor.

In those methods of treatment comprising a single dose administration protocol, a single dose of between about 0.5 mg/kg to about 50 mg/kg of a compound according to the Formula (I) or an equivalent molar amount of a pharmaceutically acceptable salt thereof is administered to the patient. In certain other single dose administration methods, a single dose comprises between about 1 mg/kg to about 25 mg/kg, between about 2 mg/kg to about 15 mg/kg of a compound of Formula I or an equivalent molar amount of a pharmaceutically acceptable salt thereof is administered to the patient. Certain preferred compounds of Formula I include NSC-281612, NSC-716794, NSC-717120, NSC-717121 and an equivalent molar amount of a pharmaceutically acceptable salt thereof.

In certain other therapeutic methods of treating renal cancer, a compound of Formula I, or a pharmaceutically acceptable salt thereof is administered to the patient suffering from or susceptible to renal cancer in two or more doses. Typically the doses are administered daily or intermittently (e.g., with at least one non-administration day separating sequential doses). In certain methods in which the compound of Formula I, or a pharmaceutically acceptable salt thereof is administered in a plurality of doses, each dose comprises between about 0.5 mg/kg and about 25 mg/kg of the compound, or more preferably, each dose comprises between about 1 mg/kg and about 15 mg/kg, or between about 2 mg/kg and about 10 mg/kg of the compound or salt of Formula I.

In certain methods in which sequential doses are administered intermittently, the sequential doses are administered between two and seven days apart. In yet other methods comprising intermittent administration of the compound or salt of Formula I, the compound is administered to the patient in three, four, five or six doses and wherein each dose is administered between three and five days apart. In yet other methods, the patient is administered four, five, or six doses administered between three and four days apart, wherein each dose comprises between about 4 mg/kg to about 8 mg/kg of 4-[bis[2-[(methylsulfonyl)oxy]ethyl]amino]-2-methyl-benzaldehyde fumarate.

In certain other therapeutic methods of treating renal cancer, the patient is administered a daily dose of a compound of Formula I, or a pharmaceutically acceptable salt thereof, for at least two days. In certain methods, the daily dose administered to the patient is between about 1 mg/kg and about 25 mg/kg, or between about 2 mg/kg and about 15 mg/kg, or between about 3 mg/kg and about 10 mg/kg. Typical daily doses administered to patients include 2 mg/kg, 4 mg/kg, 6 mg/kg, 8 mg/kg, or 10 mg/kg. Therapeutic protocols typically comprise daily administration of the compound of Formula I, or a pharmaceutically acceptable salt thereof, for between two and about fourteen days, or for between three and ten days, between about three and seven days. In certain other daily administration protocols, the compound of Formula I, or pharmaceutically acceptable salt thereof, is administered to the patient for three, four, five, six, or seven sequential days. In certain preferred methods, a dose of about 4 mg/kg to about 8 mg/kg of 4-[bis[2-[(methylsulfonyl)oxy]ethyl]amino]-2-methyl-benzaldehyde fumarate is administered daily to the patient for four, five or six consecutive days.

In certain instances, it may be desirable to conduct a plurality of intermittent administration protocols, daily administration protocols, or a combination thereof, as described above, in combination with rest and/or recovery periods. Thus, in certain instances, it may be desirable to administer a compound of Formula I, or a pharmaceutically acceptable salt thereof, such as NSC-281612, NSC-716794, NSC-717120, and/or NSC-717121, according to a daily or intermittent administration methods provided herein, measure the tumor response to the therapy, and then conduct subsequent daily or intermittent administration therapies as necessary to eliminate or further reduce the size of the renal cancer tumors.

The invention provides methods of treating patients suffering from or susceptible to renal cell carcinoma. In certain methods, the tumor to be treated is localized to one or both of the patient's kidneys. In certain other methods, the renal cell carcinoma has metastasized, e.g., at least one renal cell carcinoma tumor is present in at least one non-kidney tissue. Typically the methods provided herein are suitable for use in the treatment of patients suffering from or susceptible to renal cell carcinoma tumors which are present in the kidneys, in non-kidney tissues, or in a combination thereof.

The methods of treatment provided by the instant invention contemplate any administration pathway capable of providing a therapeutically effective dose of a compound of Formula I to the vicinity of the tumor. In certain preferred methods of treatment provided herein, the compound of Formula I, or a pharmaceutical composition comprising same is administered in a intravenously, subcutaneously, or intraperitoneally. Typically the compound of Formula I, or a pharmaceutical composition comprising same is administered intravenously or subcutaneously.

Certain exemplary methods of treating patients suffering from cancer provided herein comprise the administration of NSC-281612 to a patient suffering from renal cell carcinoma. Thus, in a murine orthotopic tumor model, a single dose, a daily dose for five days (QD×5), or a intermittent dose administered every fourth day for five total doses (Q4D×5) of NSC-281612 was administered intraperitoneally to mice previously inoculated with renal cancer cells (RXF-393). See Examples 1-2, Tables 1-3, and FIG. 1-8 of the instant invention for results of administration of NSC-281612 to mice having subcutaneous (FIG. 1) or orthotopic (FIG. 2-8) human renal cell carcinoma tumors under a variety of administration protocols and various doses.

In another aspect, the invention provides a pharmaceutical composition comprising at least one pharmaceutically acceptable carrier and a compound according to the Formula (I):

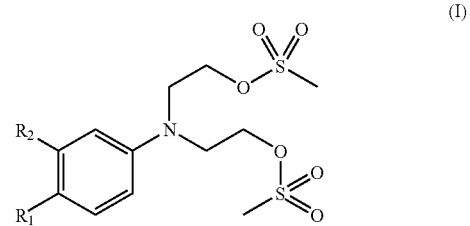

wherein $R_1$ is selected from formyl, $C_1$-$C_4$alkanoyl, $C_1$-$C_4$alkoxycarbonyl, cyano, and aldehyde O—$C_1$-$C_4$alkyloxime; and $R_2$ is selected from $C_1$-$C_4$alkyl, $C_1$-$C_4$alkoxy, and halogen, or an equivalent molar amount of a pharmaceutically acceptable salt thereof.

In certain pharmaceutical compositions, the compound of Formula I includes those compounds in which $R_2$ is selected from methyl, ethyl, methoxy, fluoro, chloro, and bromo, or $R_2$ is methyl. In other pharmaceutical compositions, the compound of Formula I includes those compounds in which $R_1$ is selected from formyl, acetyl, cyano, methoxycarbonyl, ethoxycarbonyl, and aldehyde O-methyl-oxime or $R_1$ is formyl. In certain preferred pharmaceutical compositions, the compound of Formula I includes those compounds in which $R_1$ is formyl and $R_2$ is methyl.

In certain other pharmaceutical compositions, the compound of Formula I is incorporated into the composition as a pharmaceutically acceptable salt, hydrate, or solvate. As used herein, a pharmaceutically acceptable salt is an acid or base salt that is generally considered in the art to be suitable for use in contact with the tissues of human beings or animals without excessive toxicity, irritation, allergic response, or other problem or complication. Such salts include mineral and organic acid salts of basic residues such as amines. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)_n$—COOH where n is 0-4, and the like. In certain preferred methods the patient is administered a pharmaceutically acceptable fumarate salt.

Certain pharmaceutical compositions provided herein comprise a compound of Formula I which is selected from NSC-281612, NSC-716794, NSC-717120, NSC-717121, or a pharmaceutically acceptable salt thereof. In certain other pharmaceutical compositions, the compound of Formula I is a pharmaceutically acceptable salt of 4-[bis[2-[(methylsulfonyl)oxy]ethyl]amino]-2-methyl-benzaldehyde such as 4-[bis[2-[(methylsulfonyl)oxy]ethyl]amino]-2-methyl-benzaldehyde fumarate.

The pharmaceutical compositions provided by the instant invention are suitable for use in any administration pathway contemplated by the methods of treatment in which the compositions will be used. In the methods of the invention, compounds of the invention according to Formula I and pharmaceutical compositions thereof may be administered to a subject by a variety of routes including parenteral (including intravenous, subcutaneous, intramuscular and intradermal), topical (including buccal, sublingual), oral, nasal and the like. In certain preferred pharmaceutical compositions provided herein, the pharmaceutical composition is formulated for administration by intravenous, subcutaneous, or intraperitoneal injection. Typically the pharmaceutical composition is formulated for administered by intravenous or subcutaneous injection.

In certain parenteral administration routes, the pharmaceutical composition is a sterile saline solution comprising between about 0.1 mg/mL to about 25 mg/mL of the compound of Formula I or a pharmaceutically acceptable salt thereof. Certain preferred pharmaceutical compositions for parenteral administration comprise between about 0.5 mg/mL to about 10 mg/mL of the compound of Formula I or a pharmaceutically acceptable salt thereof in a saline solution which optionally comprises one or more pharmaceutically acceptable additives.

In certain parenteral administration routes, the pharmaceutical composition is a sterile saline solution comprising between about 0.1 mg/mL to about 25 mg/mL of the compound of Formula I or a pharmaceutically acceptable salt thereof. Certain preferred pharmaceutical compositions for parenteral administration comprise between about 0.5 mg/mL to about 10 mg/mL of the compound of Formula I or a pharmaceutically acceptable salt thereof in a saline solution which optionally comprises one or more pharmaceutically acceptable additives.

In certain preferred pharmaceutical compositions, the composition comprises between about 0.25 mg to about 50 mg or between about 0.5 mg to about 25 mg of the compound according to the Formula (I) or an equivalent molar amount of a pharmaceutically acceptable salt thereof. In certain other pharmaceutical compositions of the invention, the composition comprises between about 1 mg to about 15 mg of the compound according to the Formula (I) or an equivalent molar amount of a pharmaceutically acceptable salt thereof. Yet other pharmaceutical compositions are formulated to comprise about 2 mg, about 3 mg, about 4 mg, about 5 mg, about 6 mg, about 7 mg, about 8 mg, about 9 mg, or about 10 mg of a compound of Formula I or an equivalent molar amount of a pharmaceutically acceptable salt thereof. In certain preferred formulations, the compound of formula I is selected from NSC-281612, NSC-716794, NSC-717120, NSC-717121, or a pharmaceutically acceptable salt thereof.

In certain methods of treating a patient suffering from or susceptible to cancer, the administration of the dimethane sulfonate compound (e.g., NSC-281612 or the like) to a patient suffering from or susceptible to cancer decreases tumor size by at least 50% or more preferably by at least about 60%, 70%, 80%, 90% or about 95%. In certain other methods of treating a patient suffering from or susceptible to cancer, the administration of the dimethane sulfonate compound (e.g., NSC-281612 or the like) to a patient suffering from or susceptible to cancer decreases tumor size by at least 99% or decreases tumor size until no detectable tumor remains.

Certain preferred methods of treating patients suffering from or susceptible to cancer include treatment or prevention of cancer or other tumor disorders in mammalian patients including livestock, companion animals (dogs, cats, horses and the like), primates and humans.

Treatment methods of the invention include in general administration to a patient a therapeutically effective amount of one or more compounds of Formula I. In the instant therapeutic methods, a therapeutically effective amount is sufficient to reduce the size of renal cell carcinoma tumors present in a patient or to eliminate tumors from the patient. Suitable patients include those subjects suffering from or susceptible to (i.e. prophylactic treatment) a disorder or disease identified herein. Typical patients for treatment in accordance with the invention include mammals, particularly primates, especially humans. Other suitable subjects include domesticated companion animals such as a dog, cat, horse, and the like, or a livestock animal such as cattle, pig, sheep and the like.

Preferred methods of the invention including identifying and/or selecting a subject (e.g. mammal, particularly human) that is susceptible to or suffering from a condition disclosed herein, particularly a subject that is susceptible to or suffering from one or more cancers.

A pharmaceutical composition of the invention also may be packaged together with instructions (i.e. written, such as a written sheet) for treatment of a cancer as disclosed herein, e.g. instruction for treatment of a subject that is susceptible to or suffering from cancer.

Compounds of the invention are suitably administered to a subject in a water-soluble form, e.g., as a pharmaceutically acceptable salt of an organic or inorganic acid, e.g., hydrochloride, sulfate, hemi-sulfate, phosphate, nitrate, acetate, oxalate, citrate, maleate, mesylate, etc obtained after proper chemical transformation. Also, where an acidic group is present on an inhibitor compound, a pharmaceutically acceptable salt of an organic or inorganic base can be employed such as an ammonium salt, or salt of an organic amine, or a salt of an alkali metal or alkaline earth metal such as a potassium, calcium or sodium salt. Specifically suitable pharmaceutically acceptable salts include those formed with a non-toxic cation, preferably an alkali metal cation such as K or Na, an alkaline earth metal cation such as Mg or Ca, another non-toxic metal cation such as Al or Zn or a non-toxic metalloid cation such as $NH_4^+$, piperazinium or 2-hydroxyethylammonium. Certain preferred compounds suitable for use in the methods of the invention are sufficiently water soluble in neutral for such that they may be delivered without pre-generation of a pharmaceutically acceptable salt.

Compounds suitable for use in the methods of the present invention include any and all different single pure isomers and mixtures of two or more isomers. The term isomers is intended to include diastereoisomers, enantiomers, regioisomers, structural isomers, rotational isomers, tautomers, and the like. For compounds which contain one or more stereogenic centers, e.g., chiral compounds, the methods of the invention may be carried out with a enantiomerically enriched compound, a racemate, or a mixture of diastereomers. Preferred enantiomerically enriched compounds have an enantiomeric excess of 50% or more, more preferably the compound has an enantiomeric excess of 60%, 70%, 80%, 90%, 95%, 98%, or 99% or more. In certain preferred embodiments, achiral dimethane sulfonate compounds of the invention or only a single enantiomer or diastereomer of a dimethane sulfonate compound is administered to a patient.

Compounds of the invention according to Formula I for use in the methods of the invention can be employed, either alone or in combination with one or more other therapeutic agents, as a pharmaceutical composition in mixture with conventional excipient, i.e., pharmaceutically acceptable organic or inorganic carrier substances suitable for a desired route of administration which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

For parenteral application, particularly suitable are solutions, preferably oily or aqueous solutions as well as suspensions, emulsions, or implants, including suppositories. Ampules are convenient unit dosages.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc. Tablets, capsules and syrups or other fluids are generally preferred for oral administration.

It should be understood that in addition to the ingredients particularly mentioned above the formulations of this invention may include other agents conventional in the art having regard to the type of formulation in question, for example, those suitable for oral administration may include flavoring agents.

As used herein, "alkyl" is intended to include branched, straight-chain and cyclic saturated aliphatic hydrocarbon groups including alkylene, having the specified number of carbon atoms. Examples of alkyl include, but are not limited to, methyl, ethyl, n-propyl, i-propyl, n-butyl, s-butyl, t-butyl, n-pentyl, and s-pentyl. Alkyl groups typically have 1 to about 12 carbon atoms, more typically 1 to about 8 or 1 to about 6 carbon atoms. Preferred alkyl groups are $C_{1-8}$ alkyl groups, more preferred are $C_{1-6}$-alkyl and $C_{1-4}$-alkyl groups. Especially preferred alkyl groups are methyl, ethyl, n-propyl and iso-propyl.

As used herein, the term "alkanoyl" refers to an acyl group in a linear or branched arrangement (e.g., —(C=O)-alkyl), where attachment is through the carbon of the keto group. Alkanoyl groups include $C_2$-$C_8$alkanoyl, $C_2$-$C_6$alkanoyl and $C_2$-$C_4$alkanoyl groups, which have from 2 to 8, 2 to 6 or 2 to 4 carbon atoms, respectively. "$C_1$alkanoyl" refers to —(C=O)—H, which (along with $C_2$-$C_8$alkanoyl) is encompassed by the term "$C_1$-$C_8$alkanoyl." Ethanoyl is $C_2$alkanoyl and formyl is a $C_1$alkanoyl residue.

The term "alkoxycarbonyl" refers to an alkoxy group linked via a carbonyl (i.e., a group having the general structure —C(=O)O-alkyl). Alkoxycarbonyl groups include $C_1$-$C_8$, $C_1$-$C_6$ and $C_1$-$C_4$alkoxycarbonyl groups, which have from 1 to 8, 6 or 4 carbon atoms, respectively, in the alkyl portion of the group. For example, "$C_1$alkoxycarbonyl" refers to —C(=O)—O—$CH_3$.

The term "aldehyde O-alkyl-oxime" refers to a residue of the formula, alkyl-O—N=CH—. Thus, an aldehyde O-methyl-oxime is a group of the formula Me-O—N=CH—.

The term "halogen" refers to fluoro, chloro, bromo, and iodo residues.

"Prodrugs" are intended to include any covalently bonded carriers which release the active parent drug according to Formula I in vivo when such prodrug is administered to a mammalian subject. Prodrugs of a compound are prepared by modifying functional groups present in the drug compound in such a way that the modifications are cleaved, either in routine manipulation or in vivo, to the parent compound.

Combinations of substituents and/or variables are permissible only if such combinations result in stable compounds. A stable compound or stable structure is meant to imply a compound that is sufficiently robust to survive isolation to a useful degree of purity from a reaction mixture, and formulation into an effective therapeutic agent.

According to certain embodiments, a compound of Formula I (such as NSC-281612) may be administered in combination with other compounds, including for example, chemotherapeutic agents, anti-inflammatory agents, anti-pyretic agents radiosensitizing agents, radioprotective agents, urologic agents, anti-emetic agents, and/or anti-diarrheal agents. for example, cisplatin, carboplatin, docetaxel, paclitaxel, fluorouracil, capecitabine, gemcitabine, irinotecan, topotecan, etoposide, mitomycin, gefitinib, vincristine, vinblastine, doxorubicin, cyclophosphamide, celecoxib, rofecoxib, valdecoxib, ibuprofen, naproxen, ketoprofen, dexamethasone, prednisone, prednisolone, hydrocortisone, acetaminophen, misonidazole, amifostine, tamsulosin, phenazopyridine, ondansetron, granisetron, alosetron, palonosetron, promethazine, prochlorperazine, trimethobenzamide, aprepitant, diphenoxylate with atropine, and/or loperamide.

EXAMPLES

It should be appreciated that the invention should not be construed to be limited to the example which is now described; rather, the invention should be construed to include any and all applications provided herein and all equivalent variations within the skill of the ordinary artisan.

Tumor cells (e.g., A498 and RXF-393) were derived from established tumors maintained by serial passage in mice for a maximum of 10 passages. Initial doubling times for these renal tumor xenografts were about 3.5 days and had a log linear growth rate throughout the observation period. Male mice were used in all experiments. All animals were provided by NCI contractors at the NCI-Frederick production facility or Taconic Laboratories (Germantown, N.Y.).

Intraperitoneal drug treatment schedules were established from the tumor doubling times because pharmacological data were not available. The dose levels were determined by establishing a single injection maximum tolerated dose (MTD) from which the experimental doses were calculated as: dose (mg/kg)=[(1.5×MTD)/no. of doses to be given]. Each experiment consisted of 20 control mice (based on statistical need) that received dosing vehicle (saline+0.05% Tween 80) on the same schedule as used for the test articles. Each treated group contained six mice. Tumor volumes were measured two to three times weekly and the tumor weights were calculated using the formula for a prolate ellipsoid: tumor weight (mg) ={[length (in mm)]×[width (in mm)]$^2$}/2. The control tumors reached 500 mm$^3$ in 27 days for A498 and 12 days for RXF-393.

Example 1

Subcutaneous Xenograft Tumor Model

Human tumor xenografts were generated by injection of 1×10$^7$ A498 tumor cells subcutaneously into athymic nude male mice. Four days post implantation, three doses of a pharmaceutical composition of NSC-281817 (120 mg/kg) or NSC-281612 (54 mg/kg) were administered on every fourth day (e.g., Q4D×3). Control mice were inoculated with A498 tumor cells subcutaneously and were then administered the carrier (e.g., vehicle) of the pharmaceutical composition without an anti-tumor therapeutic. The tumor weight was calculated every fourth day beginning at day 7. FIG. 1 is a plot of median tumor weight at various days post implantation for the control mice and mice administered NSC-281617 or NSC-281612. As noted, a dose of NSC-281612 was at least as effective in limiting tumor weight as NSC-281617 at double the concentration.

Example 2

Orthotopic Intrarenal Tumor Model

Female 6-8 week old SCID mice were anesthetized and placed into lateral recumbency. An incision just caudal to the left rib cage allowed exposure of the caudal pole of the kidney. The tumor cell suspension (2×10$^6$ in 0.025 mL) was slowly injected into the parenchyma of the kidney using a 27 gauge needle to minimize leakage of cells into the peritoneum. The kidney was replaced, the skin was closed and the mice recovered. Mice were randomized prior to the first treatment and then treated by various routes, doses and schedules. Controls were injected with drug vehicle (saline+0.05% Tween 80). At euthanasia (days 21-27) tumor size was determined as the difference in weight between the left (tumored) and right (non-tumored) kidneys.

An orthotopic model for renal cancer was established. Initially, RXF-393, CaKi-1 and A498 tumor cells were inoculated into the caudal pole of the kidney in athymic nude mice. Twenty-five to 35 days post-implantation representative mice were sacrificed and their kidneys collected. The weights of the inoculated and control kidney (uninoculated) were determined for each mouse. Histologic evaluations confirmed the presence of tumor in the inoculated kidney. We were unsuccessful in establishing intrarenal growth with A498 renal tumor cells. CaKi-1 did produce tumors but they were not as consistent as those generated with the RXF-393 renal tumor cells so this line was selected as the primary model for orthotopic renal tumor studies with this series of compounds.

Intermittent Intraperitoneal Administration of NSC-281612

RXF-393 cells were injected directly into the caudal pole of the kidney on Day 0. The inoculated kidney was monitored for tumor growth in treated versus control mice by collecting and weighing the kidneys on day 25 post-implantation. In a preliminary experiment, NSC-281612 was administered intraperitoneally (IP) every fourth day for a total of 5 treatments (Q4D×5) starting 4 days after tumor implantation. NSC-281612 markedly reduced the tumor burden at day 25 post-implantation. In this study, NSC-281612 was assessed at 25 mg/kg (Group 2), 16.8 mg/kg (Group 3) and 11.3 mg/kg (Group 4). Due to toxicity, the 25 mg/kg dose was lowered to 8.3 mg/kg and only 4 doses were administered to Groups 2 and 3 (see Table 1).

TABLE 1

| | |
|---|---|
| Group 1: | vehicle only Q4Dx5 IP starting day 4 post-tumor implantation. |
| Group 2: | 25 mg NSC-281612/kg Q4Dx3 and a final dose of 8.3 mg/kg IP. There was no mortality but there was a 27% average weight loss. |
| Group 3: | 16.8 mg NSC-281612/kg Q4Dx5 IP. There was no mortality but there was a 25% average weight loss. |
| Group 4: | 11.3 mg NSC-281612/kg Q4Dx5 IP. There was no mortality but there was a 20% average weight loss. |

Figure 3:
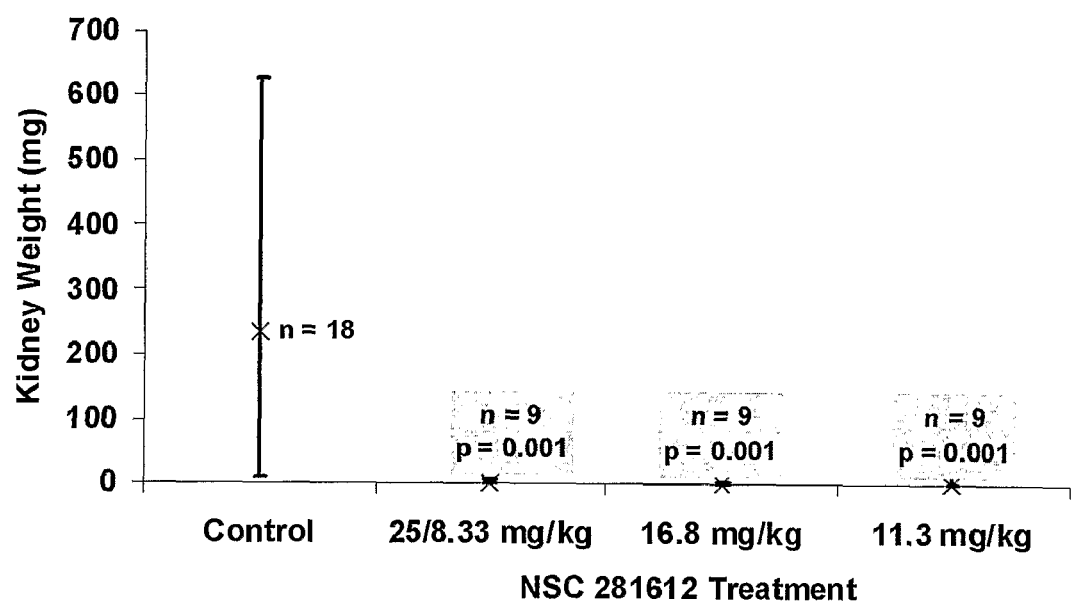
FIG. 3 is a plot of median, maximum and minimum kidney weights 25 days after implantation with RXF-393 tumor cells and administration of NSC-281612 as described in Groups I, II, III, and IV of FIG. 2.
Figure 4:
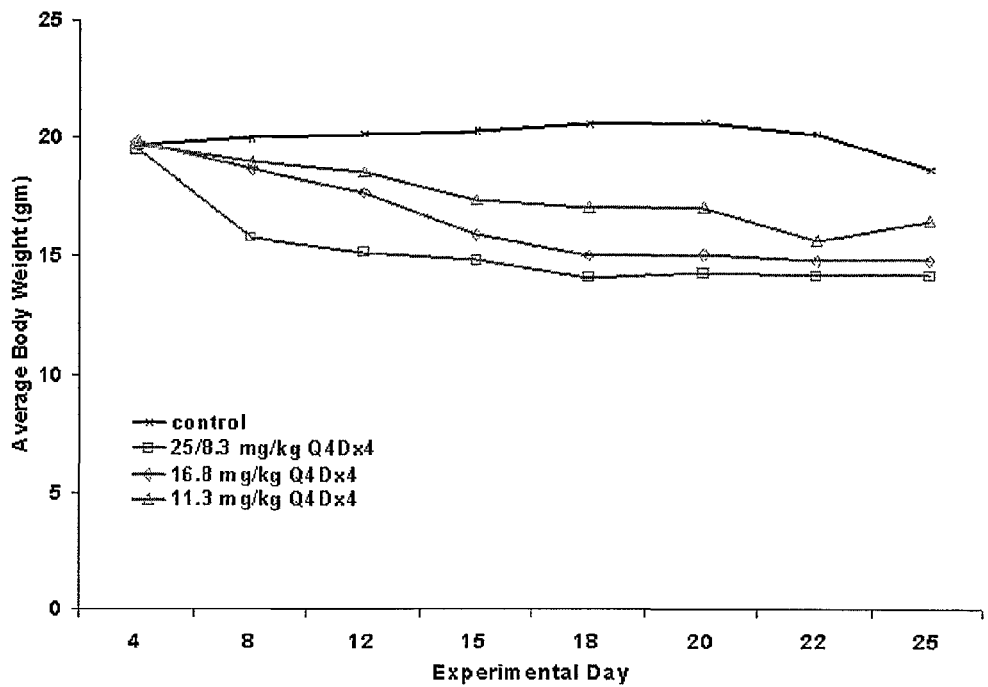
FIG. 4 is a plot of average body weight (in gms) over time from administering NSC-281612 in doses according to Groups I, II, III, and IV of FIG. 2.
Figure 5:
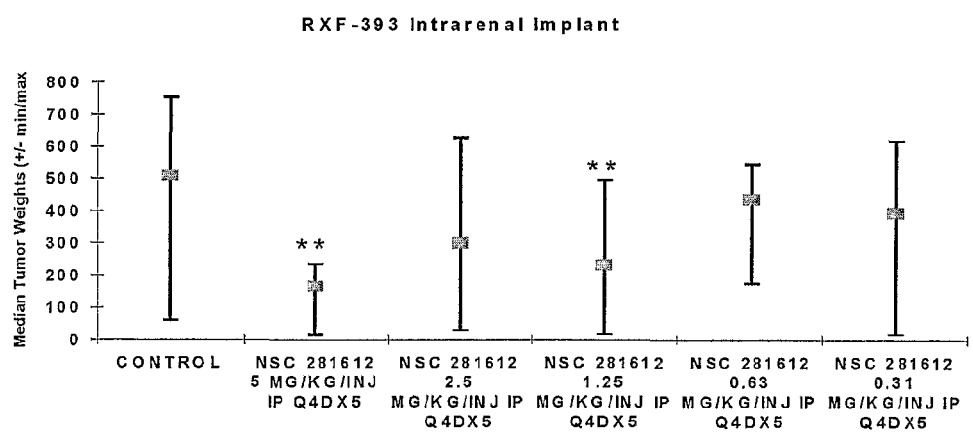
FIG. 5 is a plot of median, maximum and minimum kidney weights 25 days after implantation with RXF-393 tumor cells and administration of five doses of between 0.31-5 mg/kg/injection of NSC-281612 every fourth day starting at day 2.
Figure 6:
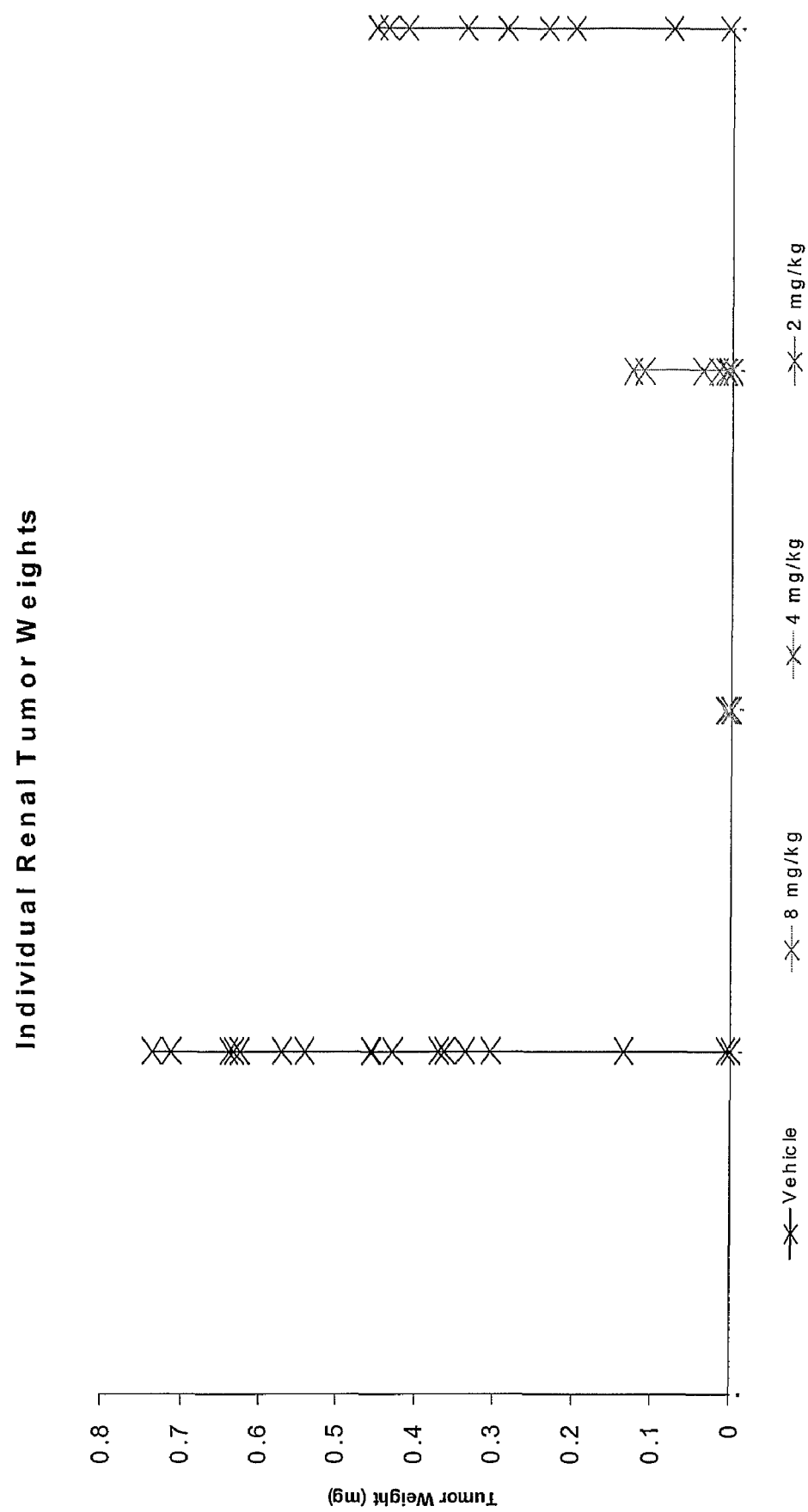
FIG. 6 is scatter plot of individual renal tumor weights 22 days after implantation with RXF-393 tumor cells and intravenous administration of five doses of 0, 2, 4, or 8 mg/kg/injection of NSC-281612 every fourth day starting at day 4.

FIG. 2A-D is a series of photographic images of representative kidneys harvested from mice of Groups 1, 2, 3, and 4. The kidney on the left in each group was the control (uninoculated) kidney while the kidney on the right was the tumor injected kidney. The tumor weight was calculated as (tumored kidney−nontumored kidney). Median, maximum and minimum kidney weights for kidneys from mice of Groups 1, 2, 3, and 4 are depicted in the graph in FIG. 3, and the effect of NSC-281612 administration on average body weight over the duration of administering NSC-281612 in Groups 1, 2, 3, and 4 is depicted in the graph in FIG. 4. FIG. 3 further provides the Student's t-test result obtained by comparing the treated and control samples. The data overwhelmingly suggested that NSC-281612 was active against intrarenal RXF-393 tumors at several doses.

A second study was conducted using the IP route of administration and the Q4D×5 dose schedule. For this the doses evaluated ranged from 5 mg/kg/dose to 0.31 mg/kg/dose. The median tumor weights (with maximum and minimum weight ranges) are presented in FIG. 5 for mice administered the control (vehicle) solution, and IP doses of 5 mg/kg/inj, 2.5 mg/kg/inj, 1.25 mg/kg/inj, 0.63 mg/kg/inj, 0.31 mg/kg/inj for five doses administered every four days starting at day four post implantation of the RXF-393 tumor cells. The 5 mg/kg/dose group did have a significant reduction in tumor mass compared to the controls but it was not as marked (no tumor free animals) as with the 11 mg/kg dose (Group 4 supra).

Intermittent Intravenous Administration of NSC-281612

To assess the impact of drug administration route, an experiment was conducted in which NSC-281612 was administered at doses of 8 mg/kg, 4 mg/kg and 2 mg/kg given intravenously (IV) on a Q4D×5 schedule with the first treatment given on day 4 post-tumor implantation. These intravenous doses were well tolerated by the mice and produced statistically significant reductions in the tumor weights at the 8 mg/kg/dose and 4 mg/kg/dose levels. The 2 mg/kg/dose intravenous treatment group did have a reduction in tumor mass; however, it did not achieve a level of statistical significance. See, Table 2 for results and FIG. 6 for individual renal tumor weights for mice administered control only (vehicle), 8 mg/kg, 4 mg/kg, or 2 mg/kg intravenously on a Q4Dx5 schedule.

TABLE 2

| Dose/Units | Day 22 median | Tumor Weight (mg) average | t-test |
|---|---|---|---|
| 0 mg/kg/dose | 455 | 418 | |
| 8 mg/kg/dose | 0 | 1 | 0.00003 |
| 4 mg/kg/dose | 7 | 31 | 0.00003 |
| 2 mg/kg/dose | 284 | 270 | 0.101 |

Single Dose Intraperitoneal Administration of NSC-281612

A single 25 mg/kg dose given to mice implanted with RXF-393 tumors was given on day 10 or 15 post-tumor implantation produced seven of ten animals with no detectable tumor whereas the same dose given on day 5 was ineffective. Results are presented in Table 3.

TABLE 3

| Grp | Dose/Units | Rt. | Schedule | Median Tumor Weight (mg, Day 27) | T/C (%) |
|---|---|---|---|---|---|
| 1 | 0 mg/kg/dose | IV | QDx1, D5 | 358 | |
| 2 | 25 mg/kg/dose | IV | QDx1, D5 | 340 | 94 |
| 3 | 25 mg/kg/dose | IV | QDx1, D10 | 0 | 0 |
| 4 | 25 mg/kg/dose | IV | QDx1, D15 | 1 | 0 |

Daily Intraperitoneal Administration of NSC-281612

A daily dose of NSC281612 administered for five sequential days provided a statistically significant decrease in tumor weight and provided tumor free animals at doses as low as 3.4 mg/kg/dose. Doses and median tumor weights are provided in Table 4. Each of the three daily dose levels reported in Table 4 provided 8 or 9 mice (out of 10 mice) without detectable renal tumors.

TABLE 4

| Grp | Dose/Units | Rt. | Schedule | Median Tumor Weight (mg, Day 23) | T/C. (%) |
|---|---|---|---|---|---|
| 1 | 0 mg/kg/dose | IV | QDx5, D5 | 392 | |
| 2 | 7.5 mg/kg/dose | IV | QDx5, D5 | 0 | 0 |
| 3 | 5 mg/kg/dose | IV | QDx5, D5 | 0 | 0 |
| 4 | 3.4 mg/kg/dose | IV | QDx5, D5 | 11.5 | 3 |

The foregoing description of the invention is merely illustrative thereof, and it is understood that variations and modifications can be effected without departing from the spirit or scope of the invention as set forth in the following claims. Each of the documents referred to herein are incorporated by reference into the disclosure of the application.

All documents mentioned herein are incorporated herein in their entirety by reference.

What is claimed is:

1. A method for treating a mammalian patient having renal cell carcinoma, comprising:
administering to the patient a compound that is a 4-[bis[2-[(methylsulfonyl)oxy]ethyl]amino]-benzaldehyde, or a pharmaceutically acceptable salt thereof, thereby treating the patient.

2. The method of claim 1, wherein the compound is a fumarate salt.

3. The method of claim 1, wherein the compound is a pharmaceutically acceptable salt of 4-[bis[2-[(methylsulfonyl)oxy]ethyl]amino]-2-methyl-benzaldehyde.

4. The method of claim 1, wherein about 4 mg/kg to about 8 mg/kg of 4-[bis[2-[(methylsulfonyl)oxy]ethyl]amino]-2-methyl-benzaldehyde fumarate is administered daily to the patient for four, five or six consecutive days.

5. The method of claim 1, wherein the renal cell carcinoma is localized to the kidney.

6. The method of claim 1, wherein the renal cell carcinoma has metastasized.

7. The method of claim 6, wherein the renal cell carcinoma is present in at least one non-kidney tissue.

8. The method of claim 1, wherein the patient is a human.

9. The method of claim 1, wherein the compound is administered intravenously, subcutaneously, or intraperitoneally.

10. The method of claim 1, wherein the compound is administered as a single dose of about 0.5 mg/kg to about 50 mg/kg.

11. The method of claim 1, wherein the compound is administered as a single dose of about 1 mg/kg to about 30 mg/kg.

12. The method of claim 1, wherein the compound is administered in two or more doses, wherein each dose comprises between about 0.5 mg/kg and about 25 mg/kg of the compound.

13. The method of claim 12, wherein sequential doses are administered between two and seven days apart.

14. The method of claim 12, wherein the compound is administered to the patient in three, four, five or six doses and wherein each dose is administered between three and five days apart.

15. The method of claim 12, wherein about 4 mg/kg to about 8 mg/kg of 4-[bis[2-[(methylsulfonyl)oxy]ethyl]amino]-2-methyl-benzaldehyde fumarate is administered to the patient in four, five or six doses and each dose is administered between three and four days apart.

16. The method of claim 1, wherein the compound is administered in two or more doses, wherein each dose comprises between about 1 mg/kg and about 15 mg/kg of the compound.

17. The method of claim 1, wherein the compound is administered in two or more doses, wherein each dose comprises between about 2 mg/kg and about 10 mg/kg of the compound.

18. The method of claim 1, wherein the compound is administered daily.

19. The method of claim 18, wherein the daily dose administered to the patient is between about 1 mg/kg and about 25 mg/kg.

20. The method of claim 18, wherein the daily dose administered to the patient is between about 2 mg/kg and about 15 mg/kg.

21. The method of claim 18, wherein the daily dose administered to the patient is between about 3 mg/kg and about 10 mg/kg.

22. The method of claim 18, wherein the compound is administered daily for between two and fourteen days.

23. The method of claim 18, wherein the compound is administered daily for between three and ten days.

24. The method of claim 18, wherein the compound is administered daily for between three and seven days.

25. The method of claim 1, wherein the compound comprises 4-[bis[2-[(methylsulfonyl)oxy]ethyl]amino]-2-methyl-benzaldehyde.

26. A method for treating a mammalian patient having renal cell carcinoma, comprising:

administering to the patient between about 0.5 mg/kg and about 25 mg/kg of 4-[bis[2-[(methylsulfonyl)oxy]ethyl]amino]-2-methyl-benzaldehyde, or a pharmaceutically acceptable salt thereof, thereby treating the patient.

27. The method of claim 26, wherein the 4-[bis[2-[(methylsulfonyl)oxy]ethyl]amino]-2-methyl-benzaldehyde is administered intravenously.

* * * * *

UNITED STATES PATENT AND TRADEMARK OFFICE
CERTIFICATE OF CORRECTION

| | | |
|---|---|---|
| PATENT NO. | : 7,989,501 B2 | Page 1 of 1 |
| APPLICATION NO. | : 12/083583 | |
| DATED | : August 2, 2011 | |
| INVENTOR(S) | : Mertins et al. | |

It is certified that error appears in the above-identified patent and that said Letters Patent is hereby corrected as shown below:

Title page, item 54 and Col. 1

"(4-[bis[2-[Methylsulfonyl)-oxy]ethyl]amino]-2-methyl-benzaldehyde),"

should read --(4-[bis[2-[(Methylsulfonyl)-oxy]ethyl]amino]-2-methyl-benzaldehyde),--

In the Specification:

Column 2, line 2, Title of application runs into column 2 and obscures the text.

Column 1, line 38, "549-860)." should read --849-860).--

Column 1, line 39, "in viva" should read --in vivo--

Column 6, line 7, "administration methods" should read --administration method--

Column 6, lines 26-27, "administered in a intravenously," should read --administered intravenously,--

Column 7, line 51, "for administered" should read --for administration--

Column 10, line 24, "—C(=O)O-alkyl)." should read -- —C(=O)-O-alkyl).--

Column 10, line 51, "agents radiosensitizing" should read --agents, radiosensitizing--

Column 10, lines 52-53, "agents. for example," should read --agents, for example,--

Column 13, line 24, "produced" should read --and produced--

Signed and Sealed this
Twentieth Day of December, 2011

David J. Kappos
*Director of the United States Patent and Trademark Office*

UNITED STATES PATENT AND TRADEMARK OFFICE
CERTIFICATE OF CORRECTION

PATENT NO. : 7,989,501 B2
APPLICATION NO. : 12/083583
DATED : August 2, 2011
INVENTOR(S) : Mertins et al.

Page 1 of 1

It is certified that error appears in the above-identified patent and that said Letters Patent is hereby corrected as shown below:

<u>On the Title Page:</u>

Item (75), under the list of Inventors, "Rao Vishnuvajjalla" should be --Rao Vishnuvajjala--.

Signed and Sealed this
Eleventh Day of June, 2013

Teresa Stanek Rea
*Acting Director of the United States Patent and Trademark Office*